(12) United States Patent
Ouchi et al.

(10) Patent No.: US 7,763,868 B2
(45) Date of Patent: Jul. 27, 2010

(54) OBJECT INFORMATION ACQUISITION APPARATUS AND OBJECT INFORMATION ACQUISITION METHOD

(75) Inventors: Toshihiko Ouchi, Sagamihara (JP); Kousuke Kajiki, Tokyo (JP); Takeaki Itsuji, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 419 days.

(21) Appl. No.: 11/869,298

(22) Filed: Oct. 9, 2007

(65) Prior Publication Data

US 2008/0116374 A1 May 22, 2008

(30) Foreign Application Priority Data

Oct. 10, 2006 (JP) .............................. 2006-275898
Jul. 18, 2007 (JP) .............................. 2007-186382

(51) Int. Cl.
*G01S 13/04* (2006.01)

(52) U.S. Cl. .................... 250/493.1; 250/225; 250/251; 340/540; 340/552; 342/22; 342/179

(58) Field of Classification Search ................ 250/225, 250/251, 493.1; 340/540, 552; 342/22, 179
See application file for complete search history.

(56) References Cited

U.S. PATENT DOCUMENTS

| | | | | |
|---|---|---|---|---|
| 5,073,782 A * | 12/1991 | Huguenin et al. | ........... | 342/179 |
| 5,227,800 A * | 7/1993 | Huguenin et al. | ........... | 342/179 |
| 6,723,991 B1 * | 4/2004 | Sucha et al. | ........... | 250/341.1 |
| 6,747,736 B2 * | 6/2004 | Takahashi | ........... | 356/319 |
| 6,777,684 B1 * | 8/2004 | Volkov et al. | ........... | 250/341.1 |
| 6,825,456 B2 * | 11/2004 | Chadwick et al. | ........... | 250/225 |
| 6,850,252 B1 * | 2/2005 | Hoffberg | ........... | 715/716 |
| 6,856,271 B1 * | 2/2005 | Hausner | ........... | 342/22 |
| 6,965,340 B1 * | 11/2005 | Baharav et al. | ........... | 342/22 |
| 6,977,379 B2 * | 12/2005 | Zhang et al. | ........... | 250/341.1 |
| 7,248,204 B2 * | 7/2007 | Lovberg et al. | ........... | 342/22 |
| 7,317,390 B2 * | 1/2008 | Huey et al. | ........... | 340/552 |
| 7,365,672 B2 * | 4/2008 | Keller et al. | ........... | 342/22 |
| 7,385,549 B2 * | 6/2008 | Lovberg et al. | ........... | 342/22 |
| 7,432,846 B2 * | 10/2008 | Martin et al. | ........... | 342/22 |
| 2003/0001558 A1 * | 1/2003 | Zhang et al. | ........... | 324/96 |
| 2004/0080448 A1 * | 4/2004 | Lovberg et al. | ........... | 342/22 |
| 2004/0155665 A1 * | 8/2004 | Arnone et al. | ........... | 324/644 |
| 2004/0252024 A1 * | 12/2004 | Huey et al. | ........... | 340/540 |
| 2004/0254463 A1 * | 12/2004 | Lehman | ........... | 600/437 |
| 2005/0087690 A1 * | 4/2005 | Usami et al. | ........... | 250/341.1 |
| 2005/0093733 A1 * | 5/2005 | Lovberg et al. | ........... | 342/22 |

(Continued)

FOREIGN PATENT DOCUMENTS

JP 2005-265793 9/2005

*Primary Examiner*—David A Vanore
(74) *Attorney, Agent, or Firm*—Fitzpartick, Cella, Harper & Scinto

(57) ABSTRACT

An object information acquisition apparatus for acquiring information on the inside of an object includes an electromagnetic wave generation unit capable of outputting a terahertz wave and of changing the output intensity, an irradiation unit that irradiates an electromagnetic wave onto an object, a scanning unit and a detection unit that detects the electromagnetic wave irradiated onto the object. The scanning unit changes the relative positions of the irradiated electromagnetic wave and the object. The detection unit detects the electromagnetic wave transmitted through or reflected by the object as a result of interaction of the object and the electromagnetic wave.

21 Claims, 9 Drawing Sheets

U.S. PATENT DOCUMENTS

| | | | |
|---|---|---|---|
| 2005/0122249 A1* | 6/2005 | Grudkowski et al. | 342/22 |
| 2005/0122257 A1* | 6/2005 | Rowe et al. | 342/179 |
| 2005/0122258 A1* | 6/2005 | Blasing et al. | 342/179 |
| 2005/0230625 A1* | 10/2005 | Zhang et al. | 250/341.1 |
| 2006/0217612 A1 | 9/2006 | Ouchi | 600/407 |
| 2006/0231762 A1* | 10/2006 | Ohtake et al. | 250/341.8 |
| 2006/0255277 A1* | 11/2006 | Cole et al. | 250/341.1 |
| 2007/0215810 A1 | 9/2007 | Kurosaka et al. | 250/358.1 |
| 2007/0252992 A1 | 11/2007 | Itsuji | 356/369 |
| 2007/0257216 A1* | 11/2007 | Withers et al. | 250/580 |
| 2007/0279136 A1 | 12/2007 | Koyama et al. | 331/107 T |
| 2007/0279143 A1 | 12/2007 | Itsuji | 331/185 |
| 2008/0048678 A1* | 2/2008 | Kurosaka et al. | 324/639 |
| 2008/0116374 A1* | 5/2008 | Ouchi et al. | 250/306 |
| 2008/0174401 A1* | 7/2008 | Reilly et al. | 340/5.2 |
| 2008/0191925 A1* | 8/2008 | Martin et al. | 342/22 |
| 2008/0210873 A1* | 9/2008 | Itsuji | 250/347 |
| 2008/0303664 A1* | 12/2008 | Huey et al. | 340/552 |
| 2008/0315098 A1* | 12/2008 | Itsuji | 250/330 |
| 2009/0041293 A1* | 2/2009 | Andrew et al. | 382/100 |
| 2009/0073023 A1* | 3/2009 | Ammar | 342/22 |
| 2009/0198466 A1* | 8/2009 | Kajiki et al. | 702/85 |

* cited by examiner

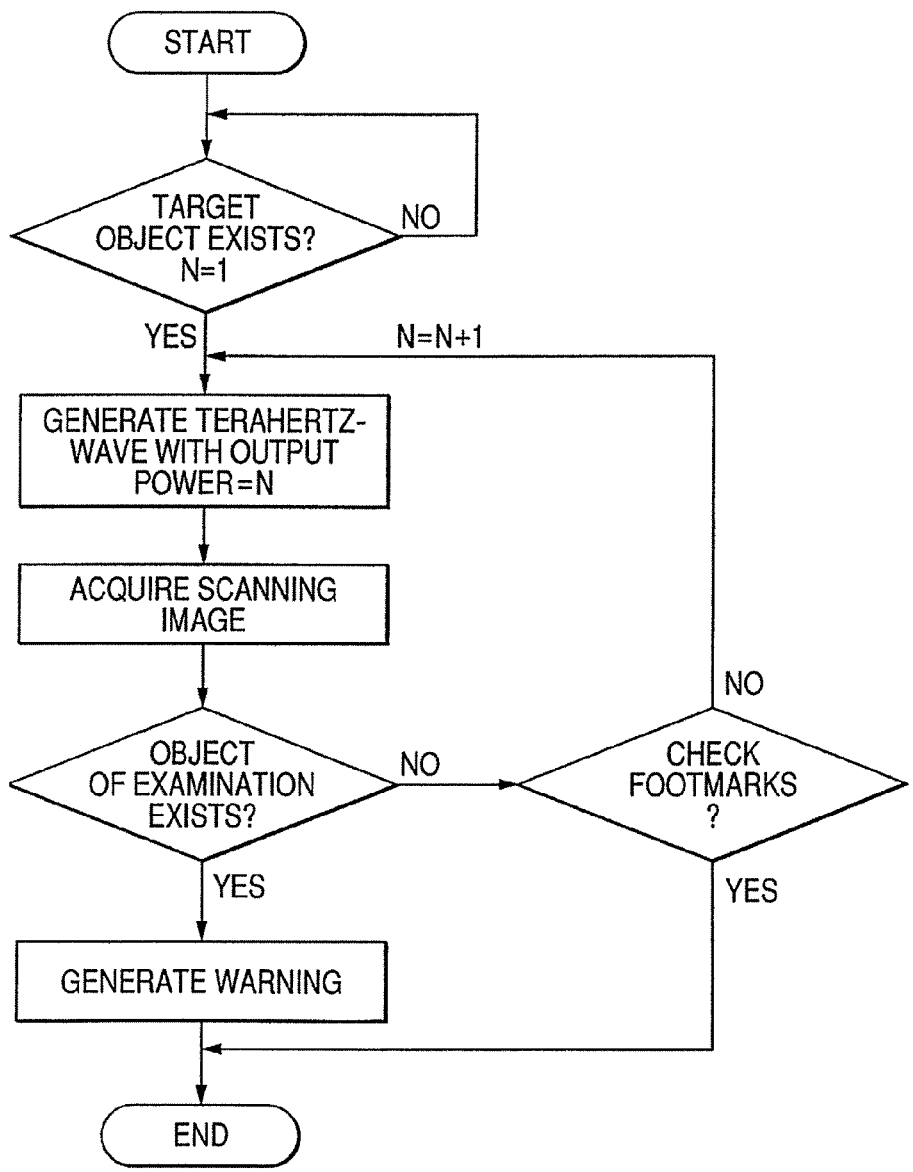

OBJECT INFORMATION ACQUISITION APPARATUS AND OBJECT INFORMATION ACQUISITION METHOD

BACKGROUND OF THE INVENTION

1. Field of the Invention

This invention relates to an object information acquisition apparatus such as an image acquisition apparatus and also to an object information acquisition method for acquiring information on an object by means of an electromagnetic wave. More particularly, the present invention relates to an image acquiring apparatus and an image acquisition method for observing the properties and the profile of an object by means of a high frequency electromagnetic wave in the domain of millimeter waves and terahertz waves (30 GHz to 30 THz).

2. Description of the Related Art

Non-destructive sensing technologies using electromagnetic waves within a range from millimeter waves to terahertz (THz)-waves (in a frequency range between 30 GHz to 30 THz, to be also referred to simply as "terahertz (THz) waves" hereafter) have been developed in recent years. Applicable fields of electromagnetic waves of the above-cited frequency band include imaging techniques for seeing-through inspections without using X-rays. Spectrometric techniques for looking into physical properties of a substance by determining the absorption spectrum and the complex permittivity of the inside of the substance, techniques for analyzing biomolecules and those for evaluating the carrier density and the mobility of a substance have also been developed.

Additionally, studies are under way to install seeing-through inspection apparatus that employs THz waves at customs inspection gates of airports in order to detect prohibited drugs and dangerous articles hidden in bags, clothes that passengers are wearing and human bodies. Particularly, techniques employing THz waves are believed to be effective for human bodies because inspections involving irradiation of X-rays entail the problem of exposure to harmful radiation. As a proposal for such a technique, a detector for determining if any prohibited drug is hidden in a human body or not by irradiating the human body with a THz wave and monitoring reflected rays has been disclosed.

As disclosed in Japanese Patent Application Laid-Open No. 2005-265793, a photoconductive switching device that is equipped with an antenna arranged on a photoconductive film formed on a substrate so as also to operate as an electrode can suitably be used as a THz wave generation unit. LT-GaAs made to grow on a GaAs substrate at low temperature can be used as a photoconductive film. $CO_2$ lasers and QC (quantum cascade) lasers can also be utilized as THz wave generations sources. However, the latter lasers cannot acquire an absorption spectrum that is specific to the object of inspection and extends over a wide frequency range, and hence the use of a plurality of THz wave generation sources of different wavelengths is necessary.

SUMMARY OF THE INVENTION

However, a detector employing a THz wave as described above requires a large THz wave output power in order to irradiate a human body and does not provide a satisfactory SN ratio with the combination of a light source of a THz wave and a sensor as described above for the background art. Additionally, such a detector requires a long integration time and hence it is not easy for the detector to inspect a human body efficiently within a short period of time. Additionally, the above patent document does not describe anything about detecting the distribution of images along the height of an object in the inside thereof so that it may obviously be difficult to detect an article hidden in a thick object such as clothing or a shoe.

Particularly, no means is currently available to irradiate a shoe sole, and so it is not possible to detect an article hidden in a shoe. Conventionally, a suspected shoe is required to be taken off and examined by means of X-rays, but this is a cumbersome operation and it is not possible satisfactorily to detect prohibited drugs and dangerous articles made of resin, particularly when they are not detectable by means of X-rays.

In view of the above-identified problems, the present invention provides an object information acquisition apparatus of the first type for acquiring information on the inside of an object, including an electromagnetic wave generation unit, an irradiation unit, a scanning unit and a detection unit. The electromagnetic wave generation unit is capable of outputting an electromagnetic wave containing a frequency component of part of the frequency range between 30 GHz and 30 THz, and changing the output intensity. The irradiation unit irradiates the electromagnetic wave to the object. The scanning unit changes the relative positions of the irradiated electromagnetic wave and the object. The detection unit detects the electromagnetic wave transmitted through or reflected by the object as a result of interaction of the object and the electromagnetic wave. Additionally, the object information acquisition apparatus is adapted to be capable of carrying out an object information acquiring operation as described below by appropriately combining the operation of changing the relative positions by the scanning unit and the operation of changing the intensity of the electromagnetic wave by the electromagnetic wave generation unit. Namely, the object information acquisition apparatus acquires tomographic information of planes of different levels in the inside of the object relative to the direction of depth thereof in the region of the object of information acquisition according to the signal detected by the detection unit.

In view of the above-identified problems, the present invention provides an object information acquisition apparatus of the second type for acquiring information on the inside of an object, including an electromagnetic wave generation unit, an irradiation unit, a scanning unit, a detection unit and a delay unit. The electromagnetic wave generation unit is capable of outputting an electromagnetic wave containing a frequency component of part of the frequency range between 30 GHz and 30 THz. The irradiation unit irradiates the electromagnetic wave to the object. The scanning unit changes the relative positions of the irradiated electromagnetic wave and the object. The detection unit detects the electromagnetic wave transmitted through or reflected by the object as a result of interaction of the object and the electromagnetic wave. The delay unit changes the delay time between the timing of outputting the electromagnetic wave of the electromagnetic wave generation unit and the timing of detecting the electromagnetic wave of the detection unit. Additionally, the object information acquisition apparatus is adapted to be capable of carrying out an object information acquiring operation as described below by appropriately combining the operation of changing the relative positions by the scanning unit and the operation of changing the delay time by the delay unit. Namely, the object information acquisition apparatus acquires tomographic information of planes of different levels in the inside of the object relative to the direction of depth thereof in the region of the object of information acquisition according to the signal detected by the detection unit.

In view of the above-identified problems, the present invention provides an object information acquisition apparatus of the third type for acquiring information on the inside of an object, including an electromagnetic wave generation unit, an electromagnetic wave bifurcation unit, an irradiation unit, a scanning unit, a delay unit, an electromagnetic wave coupling unit and a detection unit. The electromagnetic wave generation unit is capable of outputting an electromagnetic wave containing a frequency component of part of the frequency range between 30 GHz and 30 THz. The electromagnetic wave bifurcation unit bifurcates the electromagnetic wave into reference light and object light. The irradiation unit irradiates the electromagnetic wave to the object. The scanning unit changes the relative positions of the irradiated electromagnetic wave and the object. The delay unit is arranged on either or both of the light path of reference light and that of object light and changes the relative delay time between reference light and object light. The electromagnetic wave coupling unit couples object light transmitted through or reflected by the object as a result of interaction of the object and the object light and reference light provided with a relative delay time to object light by the delay unit. The detection unit detects the interference signal of reference light and object light coupled by the electromagnetic wave coupling unit. Additionally, the object information acquisition apparatus is adapted to be capable of carrying out an object information acquiring operation as described below by appropriately combining the operation of changing the relative positions by the scanning unit and the operation of changing the delay time by the delay unit. Namely, the object information acquisition apparatus acquires tomographic information of planes of different levels in the inside of the object relative to the direction of depth thereof in the region of the object of information acquisition according to the signal detected by the detection unit.

In view of the above-identified problems, the present invention provides an object information acquisition method for acquiring information on the inside of an object, including a first output step, a first scanning step, a first detection step, a second output step, a second scanning step, a second detection step, and an tomographic information acquisition step. An electromagnetic wave containing a frequency component of part of the frequency range between 30 GHz and 30 THz is output with the first output power in the first output step. The electromagnetic wave of the first output power is irradiated, while changing the relative positions thereof to the region of existence of the object, in the first scanning step. The electromagnetic wave transmitted through or reflected by the object as a result of interaction of the object and the electromagnetic wave of the first output power is detected in the first detection step. The electromagnetic wave output in the first output step is output with the second output power in the second output step. The electromagnetic wave of the second output power is irradiated, while changing the relative positions thereof to the region of existence of the object, in the second scanning step. The electromagnetic wave transmitted through or reflected by the object as a result of interaction of the object and the electromagnetic wave of the second output power is detected in the second detection step. The signal detected in the first detection step and the signal detected in the second detection step are subjected to a process including an arithmetic process of the variations of the both signals and tomographic information of the plane of a predetermined level relative to the direction of internal depth of the object within the region of the object of information acquisition is acquired in the tomographic information acquisition step. This object information acquisition method is an example of information acquisition method of the first type that can be executed in an object information acquisition apparatus of the first type according to the present invention. The number of output steps, that of scanning steps and that of detection steps may be increased to three or more than three.

In view of the above identified problems, the present invention provides an object information acquisition method for acquiring information on the inside of an object, including an output step, a scanning step, a detection step and a tomographic information acquisition step. An electromagnetic wave containing a frequency component of part of the frequency range between 30 GHz and 30 THz is output in the output step. The electromagnetic wave is irradiated, while changing the relative positions thereof to the region of existence of the object, in the scanning step. The electromagnetic wave is fixed at each scanning position of the scanning step, while the output power of the electromagnetic wave is made to vary from a predetermined output power, and the electromagnetic wave transmitted through or reflected by the object as a result of interaction of the object and the electromagnetic wave is detected in the detection step. The signal detected in the detection step is subjected to a process including an arithmetic process of the variations of the signal and tomographic information of at least the plane of a level relative to the direction of internal depth of the object within the region of the object of information acquisition is acquired in the tomographic information acquisition step. This object information acquisition method is an example of information acquisition method of the second type that can be executed in an object information acquisition apparatus of the first type according to the present invention.

In view of the above-identified problems, the present invention provides an object information acquisition method for acquiring information on the inside of an object, including a first output step, a first scanning step, a first detection step, a second output step, a second scanning step, a second detection step and an tomographic information acquisition step. An electromagnetic wave containing a frequency component of part of the frequency range between 30 GHz and 30 THz is output with a predetermined output power in the first output step. The electromagnetic wave of the first output step is irradiated, while changing the relative positions thereof to the region of existence of the object, in the first scanning step. The delay time between the timing of outputting the electromagnetic wave and the timing of detecting the electromagnetic wave is defined as the first time at each scanning position of the first scanning step and the electromagnetic wave transmitted through or reflected by the object as a result of interaction of the object and the electromagnetic wave is detected in the first detection step. The electromagnetic wave output in the first output step is output with the predetermined output power in the second output step. The electromagnetic wave of the second output step is irradiated, while changing the relative positions thereof to the region of existence of the object, in the second scanning step. The delay time between the timing of outputting the electromagnetic wave and the timing of detecting the electromagnetic wave is defined as the second time at each scanning position of the second scanning step and the electromagnetic wave transmitted through or reflected by the object as a result of interaction of the object and the electromagnetic wave is detected in the second detection step. The signal detected in the first detection step and the signal detected in the second detection step are processed and tomographic information of the planes of different levels relative to the direction of internal depth of the object within the region of the object of information acquisition is acquired in the tomographic information acquisition step. This object information acquisition method is an example of information acquisition method of the first type that can be executed in an object information acquisition apparatus of the second type according to the present invention. The number of output steps, that of scanning steps and that of detection steps may be increased to three or more than three.

In view of the above-identified problems, the present invention provides an object information acquisition method for acquiring information on the inside of an object, including an output step, a scanning step, a detection step and a tomographic information acquisition step. An electromagnetic wave containing a frequency component of part of the frequency range between 30 GHz and 30 THz is output with a predetermined output power in the output step. The electromagnetic wave is irradiated, while changing the relative positions thereof to the region of existence of the object, in the scanning step. In the detection step, the delay time between the timing of outputting the electromagnetic wave and the timing of detecting the electromagnetic wave is changed from a predetermined time stepwise at each scanning position of the scanning step and the electromagnetic wave transmitted through or reflected by the object as a result of interaction of the object and the electromagnetic wave is detected at each time of changing the delay time. The signal detected in the detection step is processed and tomographic information of at least the plane of a level relative to the direction of internal depth of the object within the region of the object of information acquisition is acquired in the tomographic information acquisition step. This object information acquisition method is an example of information acquisition method of the second type that can be executed in an object information acquisition apparatus of the second type according to the present invention.

In view of the above-identified problems, the present invention provides an object information acquisition method for acquiring information on the inside of an object, including a first output step, a first scanning step, a first detection step, a second output step, a second scanning step, a second detection step and an tomographic information acquisition step. An electromagnetic wave containing a frequency component of part of the frequency range between 30 GHz and 30 THz is output with a predetermined output power in the first output step. Object light produced by bifurcating the electromagnetic wave of the first output step is irradiated, while changing the relative positions thereof to the region of existence of the object, in the first scanning step. The delay time between reference light and object light produced by bifurcating the electromagnetic wave is defined as the first time at each scanning position and then the interference signal of reference light and object light produced as a result of coupling object light transmitted through or reflected by the object as a result of interaction of the object and object light and reference light provided with a relative delay time is detected in the first detection step. The electromagnetic wave output in the first output step is output with the predetermined output power in the second output step. Object light produced by bifurcating the electromagnetic wave of the second output step is irradiated, while changing the relative positions thereof to the region of existence of the object, in the second scanning step. The delay time between reference light and object light produced by bifurcating the electromagnetic wave is defined as the second time at each scanning position of the second scanning step and then the interference signal of reference light and object light produced as a result of coupling object light transmitted through or reflected by the object as a result of interaction of the object and object light and reference light provided with a relative delay time is detected in the second detection step. The signal detected in the first detection step and the signal detected in the second detection step are processed and tomographic information of the planes of different levels relative to the direction of internal depth of the object within the region of the object of information acquisition is acquired in the tomographic information acquisition step. This object information acquisition method is an example of information acquisition method of the first type that can be executed in an object information acquisition apparatus of the third type according to the present invention. The number of output steps, that of scanning steps and that of detection steps may be increased to three or more than three.

In view of the above-identified problems, the present invention provides an object information acquisition method for acquiring information on the inside of an object, including an output step, a scanning step, a detection step and a tomographic information acquisition step. An electromagnetic wave containing a frequency component of part of the frequency range between 30 GHz and 30 THz is output with a predetermined output power in the output step. Object light produced by bifurcating the electromagnetic wave of the output step is irradiated, while changing the relative positions thereof to the region of existence of the object, in the scanning step. The relative delay time between reference light and object light produced by bifurcating the electromagnetic wave is changed from a predetermined time at each scanning position of the scanning step and then the interference signal of reference light and object light produced as a result of coupling object light transmitted through or reflected by the object as a result of interaction of the object and object light and reference light provided with a relative delay time is detected at each time of changing the relative delay time in the detection step. The signal detected in the detection step is processed and tomographic information of at least the plane of a level relative to the direction of internal depth of the object within the region of the object of information acquisition is acquired in the tomographic information acquisition step. This object information acquisition method is an example of information acquisition method of the second type that can be executed in an object information acquisition apparatus of the third type according to the present invention.

Thus, according to the present invention, tomographic information of an object such as a tomographic image is acquired by combining scanning only a necessary region with a THz-wave beam relatively having penetrating power and changing the intensity of the THz wave stepwise. Additionally, according to the present invention, tomographic information of an object such as a tomographic image is acquired by combining scanning only a necessary region with a THz-wave beam relatively having penetrating power and detecting the difference of arrival time, the intensity and so on of an electromagnetic wave by a detection unit. Therefore, it is possible to appropriately converge a THz beam and quickly and relatively easily acquire information on an object typically in the form of transmission images or reflection images at different levels in the direction of depth of the inside of the object with a satisfactory SN ratio and to detect an object that is not visible from the surface of another object hiding the object.

Further features of the present invention will become apparent from the following description of exemplary embodiments with reference to the attached drawings.

BRIEF DESCRIPTION OF THE DRAWINGS

FIG. 2 is a flowchart of the operation of an embodiment and an example of object information acquisition apparatus according to the present invention.

DESCRIPTION OF THE EMBODIMENTS

Figure 1A:
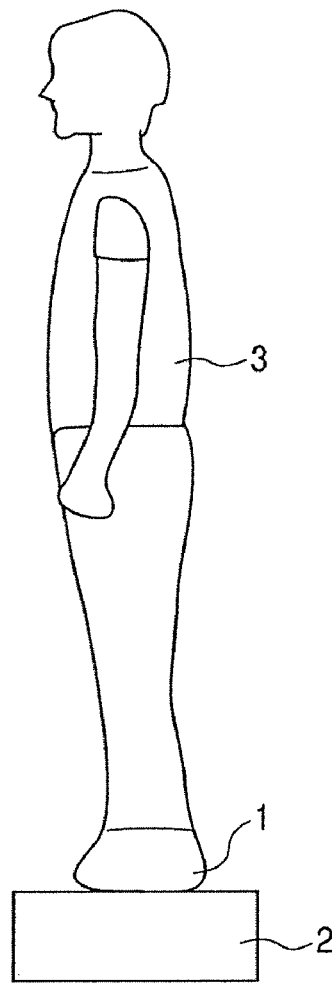
FIGS. 1A and 1B are schematic illustrations of an embodiment of object information acquisition apparatus according to the present invention.
Figure 1B:
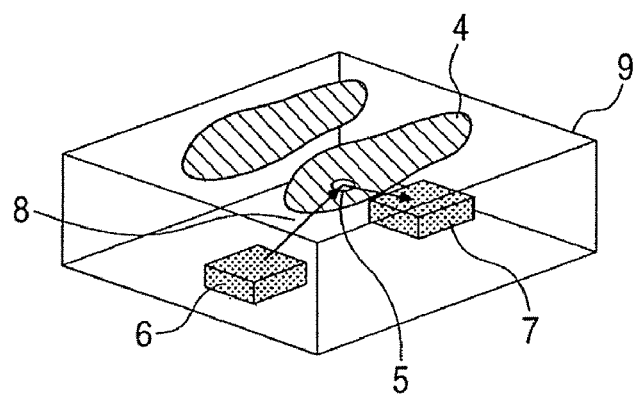

Now, an embodiment of the present invention will be described below. FIGS. 1A and 1B schematically illustrate an embodiment of object information acquisition apparatus according to the present invention, where an object information acquisition method according to the invention operates and which is a shoe sole sensor where a corresponding shoe sole sensing method operates. With the shoe sole sensor, or the image acquisition apparatus, a person 3 wearing shoes 1 steps upon the sensor 2 that is typically placed on a passageway and stands still there. The sensor 2 may be simply placed on the passageway floor, or buried in the floor of the passageway to make the sensor flush with the floor.

FIG. 1B schematically illustrates the internal structure of the shoe sole sensor 2 of this embodiment. A pressure sensor (not illustrated) that is a detection unit is bonded to a member typically made of a resin material (such as polyethylene) that is transparent relative to terahertz waves on the surface 9 of the apparatus. The pressure sensor detects the region of the object of which property information is to be acquired on the basis of the pressure change that takes place in the part where the object is present. Thus, it is possible to detect the region 4 where the person 3 steps as a footprint with this arrangement. As the pressure sensor senses that the person 3 steps upon the surface 9, terahertz-wave generator 6 that is used here as an electromagnetic wave generation unit irradiates the region 4 sensed by the pressure sensor with a terahertz-wave beam 8, two-dimensionally scanning the region. The electromagnetic wave generation unit can output an electromagnetic wave containing a frequency component of part of the frequency range between 30 GHz and 30 THz. Typically an about 6 mmφ spot 5 of a terahertz wave is irradiated onto the shoe soles found in the region 4 and the reflected wave thereof enters detector (detection unit) 7 and is detected. The reflected wave is produced because a terahertz wave is reflected at the boundary of media on or in the shoe sole. While a terahertz wave is irradiated only onto the region 4 sensed by the pressure sensor in the above description, a fixed region to be scanned may be defined in advance to eliminate the unit, or the pressure sensor, for detecting the region that needs to be scanned by a terahertz wave.

A biaxial galvanomirror or a MEMS (micro electro-mechanical systems) mirror that oscillates two-dimensionally may be used as a scanning unit for two-dimensionally scanning a terahertz wave to change the relative positions of the irradiated electromagnetic wave and the object of scanning. An optical system having an area of appropriate dimensions may be arranged between the apparatus surface 9 and the detector 7 in order to guide the reflected wave reflected by the two-dimensionally scanned shoes 1 to the detector 7. The light receiving area of the detector 7 may be so selected as to be sufficient for reliably receiving the reflected wave of the two-dimensionally scanning wave.

FIG. 2 is a flowchart of a typical operation of the shoe sole sensor 2 of this embodiment. As a person (object of examination) is not on the surface 9 of the apparatus and hence no pressure is applied there, the terahertz wave generator 6 does not generate any terahertz wave and hence is in a standby state. As the pressure sensor senses pressure, a terahertz wave is generated, but the generation output power can be increased or changed stepwise. Initially, the generation output power is the minimum output power (N=1). Examples of devices that can be used for the terahertz-wave generator 6 include a parametric generator, a backward traveling wave oscillator, a quantum cascade laser, a resonant tunneling diode and a photoconductive switching device.

The terahertz wave output power is maximally 30 mW in the case of a quantum cascade laser. Typically, it is so arranged that the terahertz wave output power N can be increased stepwise with a step of 100 nW, although the present invention is by no means limited thereto. When a quantum cascade laser is used, the output power can be adjusted by adjusting the magnitude of the injection current or the pulse drive duty ratio. In the case of generators of other types, an attenuator may be arranged upstream relative to the generator to adjust the output power.

Each time the initial output power of the terahertz wave is changed stepwise on a step-by-step basis, the terahertz-wave beam is irradiated two-dimensionally and signal obtained by the detector 7 is processed appropriately to obtain information on the tomographic images of the different levels of the inside of each of the shoe soles. Thus, the first output step of outputting the electromagnetic wave with the first output power, the first scanning step of irradiating the object with the electromagnetic wave, the second output step of outputting the electromagnetic wave with the second output power and the second scanning step of irradiating the object with the electromagnetic wave are executed sequentially. Then, tomographic information of a predetermined level relative to the direction of internal depth of the object is acquired in the tomographic information acquisition step. It may be so arranged that the reaction characteristics of each of a number of specific drug may be stored in a memory in advance and compared with the acquired information for agreement and a warning is issued when there is an agreement for a reaction.

When the reflected wave is detected in this embodiment, tomographic image information of planes of different levels in the inside of the object relative to the direction of depth thereof of the object (which is shoes 1 in this case) is acquired in a manner as described below. The object is scanned with a terahertz-wave beam of a certain output power level and the signal of the reflected light of each scanned area is detected and stored in a memory. Then, a terahertz-wave beam is generated with an output power level that is raised by a step from the former output power level and the object is scanned similarly with the terahertz-wave beam. The signal of the reflected light of each scanned area is detected by the detector 7 and stored in the memory. The terahertz-wave beam whose output power level is raised by a step penetrates the object deeper by a step and the number of signals of the reflected light from the different levels in the inside of the object is increased if compared with the number of signals detected before penetrating the object deeper by a step. Then, the variation of the latter signal from the former signal of each scanned area is arithmetically processed and the outcome of the arithmetic process is plotted so as to correspond to the scanned area. With this arrangement, it is possible to acquire tomographic image information of the plane of the penetrated level of the latter terahertz-wave beam in the object. As this process is executed each time a beam scanning operation is completed after raising the output power level by a step, it is possible to acquire information on a plurality of tomographic images that correspond to the different levels in the inside of the object relative to the direction of depth thereof. The images can be acquired by using the time differences (which arise due to the differences of refractive index of the media in the inside of the object) or the intensity differences (which arise due to the differences of absorption coefficient of the media in the inside of the object) of the peaks of the plurality of THz pulse wave signals that correspond to the respective scanning areas of the plane of each level. This imaging technique can be used in other embodiments of information acquisition method according to the present invention.

The oscillation frequency of the THz-wave can be defined in a frequency band that shows a high absorption level relative to the specific drug that needs to be checked for. The terahertz-wave output power is started from the minimum output power level and, if no reaction is detected, the output power N is raised stepwise on a step-by-step basis in order to sequentially acquire two-dimensional images of the terahertz wave of the planes of different levels in the inside of the object relative to the direction of depth thereof in order to see if a specific object exists in the object or not.

Figures 3A, 3B, 3C, 3D:
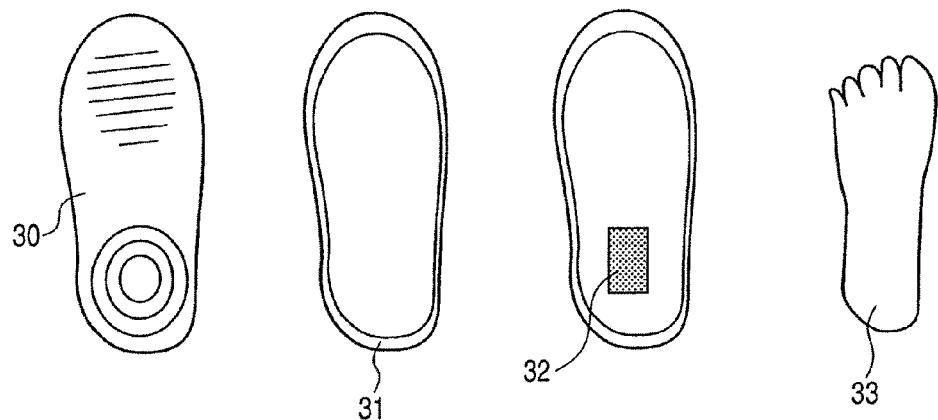
FIGS. 3A, 3B, 3C and 3D are schematic tomographic images of the sole of a shoe.

FIGS. 3A through 3D are schematic tomographic images of the sole of a shoe that change as a function of the increase of the terahertz wave output power. FIG. 3A illustrates that the undulation pattern 30 formed on the shoe sole is visible. As the output power is raised, the edge 31 or the lateral surface of the shoe is observed as illustrated in FIG. 3B. When something is hidden in the shoe sole, an article indicated by reference symbol 32 and having a strange profile that is not related to the shoe is observed as illustrated in FIG. 3C. As the output power is raised still further, the profile of a foot 33 as shown in FIG. 3D becomes visible. The inspection is terminated as normal without any problem when no abnormal reaction is found until an image as illustrated in FIG. 3D is acquired (see the flowchart of FIG. 2). However, it may be so arranged that the sensor issues a warning when the person on the shoe sole sensor 2 moves the feet and the profiles of the feet change.

Figure 4:
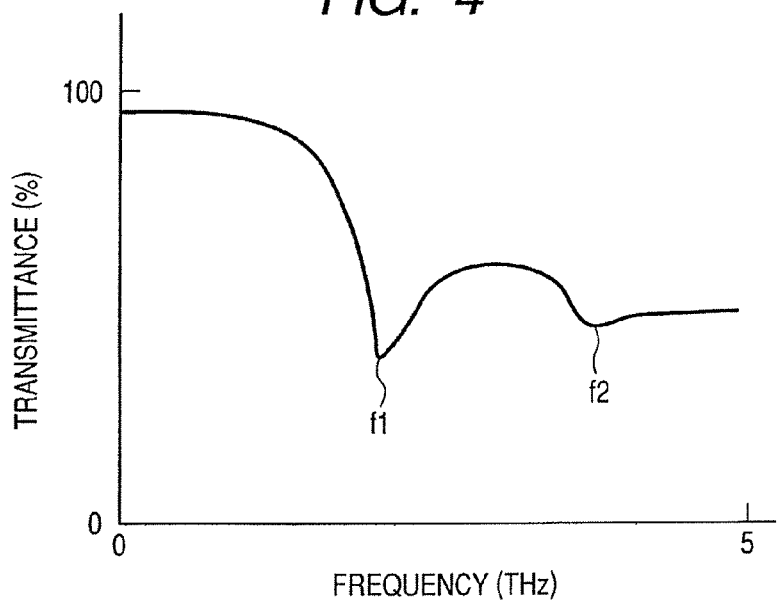
FIG. 4 is a schematic illustration of a transmission spectrum of an object.

It may be so arranged, when an article indicated by reference symbol 32 and having a strange profile as illustrated in FIG. 3C is detected, a terahertz wave having a frequency different from the first terahertz wave is irradiated only onto the part of the reference symbol 32 from the terahertz-wave generator to see the reflection characteristics of the article. Assume here that the terahertz wave that is irradiated first has frequency f1 and the terahertz wave that is irradiated after detecting an article having a strange profile has frequency f2. When the specific substance to be checked illustrates spectrum characteristics as illustrated in FIG. 4, the specific substance can be identified by computing the ratio of the transmittance of f1 and that of f2. When the spectrum characteristics satisfy specific requirements, the shoe sole sensor 2 issues a warning that the person has the specific substance, and the examination ends. With the above-described arrangement, the electromagnetic wave generation unit needs to be provided with two coherent light sources that oscillate with respective single frequencies that are different from each other in the frequency range between 30 GHz and 30 THz. When such is the case, at least one of the frequencies is made to correspond to one of the frequencies of the absorption spectrum that the specific substance to be detected such as a prohibited drug characteristically shows.

With the above-described arrangement, it is possible to avoid an error operation when output fluctuations arise for some other reason. Such a spectrum for a specific frequency in the terahertz-wave range is referred to as a "fingerprint" spectrum and is specific to a substance, which may be a prohibited drug. Each of many different substances can be identified when such information is stored in a database of the apparatus and associated with each detection of the information. When an article showing a strange profile can be identified as a prohibited belonging such as a knife or a gun from the acquired image, it may be so arranged as to issue a warning before irradiating an electromagnetic wave with the frequency f2. More specifically, the examination may be terminated when an article having a strange profile as indicated by reference symbol 32 in FIG. 3C is detected and a warning is issued by a transmission unit (see the flowchart of FIG. 2). This is based on that, when an object having a permittivity different from the shoe sole is hidden, the reflection intensity thereof differs from the shoe sole so that it is possible to acquire the profile of the object. Thus, it is possible to know the existence of an article that is the target of inspection and contained in the inside of an object by seeing the profile thereof and also by comparing the spectrum thereof with the spectrum information stored in the database of the apparatus. Either detection process may be selectively used depending on the situation.

When detecting the transmitted wave of an object, tomographic image information that corresponds to the different levels in the inside of the object relative to the direction of internal depth of the object is acquired in a manner as described below. A terahertz-wave beam of a certain output power level is irradiated for scanning and the signal of the transmitted light at each of the scanned areas is detected by means of a detector and stored. Then, a terahertz-wave beam is generated and irradiated for scanning with an output power level that is reduced from the first terahertz-wave beam by a step and the signal of the transmitted light at each of the scanned areas is detected by means of the detector and stored. Then, the former signal and the latter signal are subjected to an arithmetic process at each of the scanned areas and the results of the arithmetic processes are plotted in association with the scanned areas to obtain tomographic image information sequentially from the plane of the level remote from the transmitting side of the terahertz-wave beams in the inside of the object. This is because the pulses of reflected light that come out from the object after experiencing internal absorption are sequentially reduced from the plane of the level remote from the transmitting side of the terahertz-wave beams in the inside of the object as the output power level is reduced. As the process is executed, for instance, each time when a beam scanning operation is completed while the output power level is reduced by a step each time, it is possible to acquire tomographic image information of a plurality of tomographic images of the planes of different levels in the inside of the object relative to the direction of internal depth of the object. The above described mode of carrying out the object information acquisition method according to the invention and adapted to detect reflected light or transmitted light corresponds to the first type of information acquisition method of the invention that can be executed in an object information acquisition apparatus of the first type according to the present invention.

With a method of irradiating a photoconductive switching device with a femtosecond laser to generate a terahertz-wave pulse, it is not necessary to specify a particular oscillation wavelength because the frequency range is broad. In such a case, additionally, the delay time of the femtosecond laser that is made to enter the detector is defined to a predetermined value and signal information is acquired from the plane of the corresponding level in the inside of the object. Then, signal information is acquired from the planes of different levels in the inside of the object by changing the predetermined value of the delay time between the timing of outputting an electromagnetic wave from the electromagnetic wave generation unit and the timing of detecting the electromagnetic wave by means of the detection unit. On the other hand, the output of the terahertz-wave beam with which the object is irradiated is held to a constant level throughout all the scanning operations regardless if reflected light or transmitted light from the object is detected because the transmitted wave includes the signal waves reflected at the planes of different levels in the inside of the object with different propagation delay times. Then, the detector detects light of either the reflected wave pulse or the transmitted wave pulse of each of the different propagation delay times by adjusting the delay time of the femtosecond laser in each scanning operation to acquire image information of each of the planes of different levels in the inside of the object. Thus, for example, the first detection step of defining the delay time to the first value and detecting the electromagnetic wave from the object and the second detection step of defining the delay time to the second value and detecting the electromagnetic wave from the object are executed in this way. Then, tomographic information of the plane of a predetermined level relative to the direction of internal depth of the object is acquired in the tomographic information acquisition step. This mode of carrying out the object information acquisition method according to the invention corresponds to the first type of information acquisition method of the invention that can be executed in an object information acquisition apparatus of the second type according to the present invention.

An embodiment including an electromagnetic wave bifurcation unit, a delay unit, an electromagnetic wave coupling unit and a detection unit is also feasible. With such an arrangement, the electromagnetic wave bifurcation unit bifurcates the electromagnetic wave into reference light and object light. The delay unit is arranged at least on either the light path of reference light and that of object light and changes the relative delay time between reference light and object light. Then, the electromagnetic wave coupling unit couples object light transmitted through or reflected by the object as a result of interaction of the object and the object light and reference light provided with a relative delay time relative to object light. The detection unit detects the interference signal of reference light and object light that are coupled with each other. The detecting operation is conducted for a plurality of times with the differently defined delay times. Then, it is possible to acquire tomographic information of the planes of different levels in the inside of the object relative to the direction of depth thereof in the region of the object for acquiring information thereof according to the signal detected in each detection step. This mode of carrying out the object information acquisition method according to the invention corresponds to the first type of information acquisition method of the invention that can be executed in an object information acquisition apparatus of the third type according to the present invention.

With the above described embodiment, it is possible to examine if a person has a dangerous material or not in a simple manner without forcing the person to take off the shoes.

An object is scanned entirely to acquire tomographic image information of the plane of a level in the inside of the object, and then the object is scanned entirely again with an output power level varied from that of the first scanning operation to acquire tomographic image information of the plane of the next level in the inside of the object in the above description. Thereafter, the above operation is repeated if necessary. However, there are other feasible modes of carrying out the method of the present invention. For example, the output power level of the irradiating terahertz wave is changed stepwise in a scanning area to acquire image information of the planes of different levels of that area. Then, an adjacent scanning area is selected and the output power level of the irradiating terahertz wave is changed in a similar manner to acquire image information of the planes of different levels of that area. Then, the above operation is repeated, and finally an appropriate process is executed to acquire overall tomographic image information of the planes of different level. This mode of carrying out the object information acquisition method according to the invention corresponds to the second type of information acquisition method of the invention that can be executed in an object information acquisition apparatus of the first type according to the present invention. Of course, it is also possible to combine an operation of changing the relative positions by the scanning unit and the operation of changing the intensity of the electromagnetic wave by the electromagnetic wave generation unit to acquire tomographic information of the planes of different levels relative to the direction of internal depth of the object.

When acquiring tomographic image information of the planes of different levels at the detector side by using a terahertz-wave pulse, controlling the above described delay time, it is also possible to operate in the mode of acquiring image information of the planes of different levels of each scanning area, changing the delay time stepwise. This mode of carrying out the object information acquisition method according to the invention corresponds to the second type of information acquisition method of the invention that can be executed in an object information acquisition apparatus of the second type according to the present invention.

When detecting the interface signal of reference light and object light by means of an electromagnetic wave bifurcating unit and an electromagnetic wave coupling unit, it is also possible to operate in the mode of acquiring image information of the planes of different levels of each scanning area, changing the delay time stepwise in each scanning area. This mode of carrying out the object information acquisition method according to the invention corresponds to the second type of information acquisition method of the invention that can be executed in an object information acquisition apparatus of the third type according to the present invention.

Thus, with the above-described embodiment, it is possible to relatively easily acquire information on an object typically in the form of transmission images or reflection images at different levels in the direction of depth of the inside of the object with a satisfactory SN ratio and to detect an object that is not visible from the surface of another object hiding the object. When the electromagnetic wave generation unit is a device that can be downsized, the configuration of the entire apparatus can be simplified and hence the apparatus can be downsized. Therefore, an image acquisition apparatus such as a THz imaging apparatus can find a broadened scope of application and can be installed in airports, in various other transportation systems and in various distribution systems as industrial products for examining articles.

EXAMPLES

Now, the present invention will be described further by way of examples, referring to the drawings.

Example 1

Figure 5:
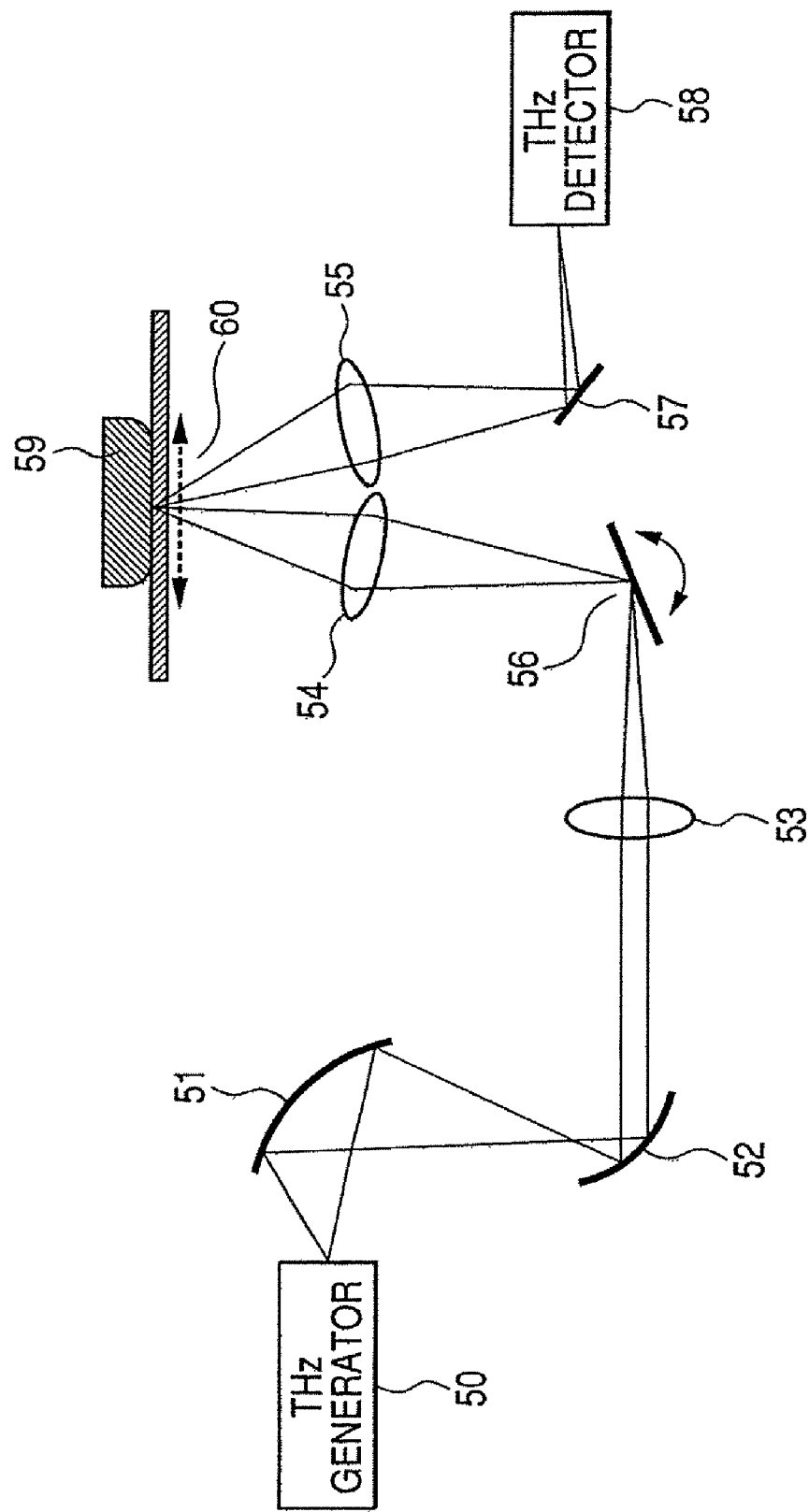
FIG. 5 is a schematic illustration of the object information acquisition apparatus of Example 1 according to the present invention.

FIG. 5 is a schematic illustration of the image acquisition apparatus of Example 1 according to the present invention, which is a shoe sole sensor, illustrating the specific configuration thereof. In FIG. 5, 50 denotes a relatively high (not less than the order of nW) output coherent continuous THz-wave generator, which is an AlGaAs/GaAs type quantum cascade laser in this example, although the present invention is by no means limited thereto. For example, a parametric oscillator using nonlinear optical crystal or a backward traveling wave oscillator may alternatively be used. The generator can generate a THz-wave with an output level of 30 mW and an oscillation frequency of about 3 THz as it is cooled to the temperature of liquid nitrogen. The generated THz-wave is collimated to a parallel beam of light with a beam diameter of about 12 mm by means of paraboloidal mirrors 51, 52 and converged to irradiate the sole of shoe 59, which is the object of examination, by means of lenses 53, 54. A biaxial galvanomirror 56 that operates as two-dimensional deflector is employed to two-dimensionally scan the sole of the shoe 59 supported on a supporting surface as indicated by reference symbol 60.

The THz-wave that is reflected by the shoe sole is detected by THz-wave detector 58 by way of lens 55 and reflector mirror 57. The detector 58 synthesizes a two-dimensional tomographic image of the plane of each level as viewed in the direction of the depth of the inside of the shoe 59. A pyroelectric detector that is typically formed by using DLATGS (deuterated L-alanine doped triglycene sulphate) crystal was used in this example. However, the detector that can be used for the purpose of the present invention is by no means limited thereto and a bolometer, a Schottky diode or a Golay cell may alternatively be used.

As illustrated in the flowchart of FIG. 2, which is already described above, after acquiring a piece of scanning image information, the output power N of the THz-wave is gradually raised stepwise on a step-by-step (unit by unit) basis. In this example, after each cycle of acquiring a piece of scanning image information, the output power is raised by a step of 100 μW and the examination of the shoe sole is terminated typically when the output power is raised to about 20 W. With this technique of beam scanning, the ability of the THz-wave of penetrating into a substance is improved (and hence the depth of penetration into a substance is increased each time the output power is raised) to by turn improve the SN ratio of the acquired image because the power of the THz wave is concentrated. Here again, the information obtained by arithmetically processing the detection signals acquired with output the power that is raised step-by-step is taken in from each scanned area and plotted so as to correspond to the scanned area.

In this example, since a THz-wave is adapted to irradiate only one or more than one areas for a duration of time necessary for the examination, it is possible to minimize the power consumption and the examination time. In this way, it is possible to examine the object (if any) that is hidden in the shoe sole and acquire information on the object (including the profile and the identity of the object) as described above by referring to an embodiment.

Example 2

Figure 6:
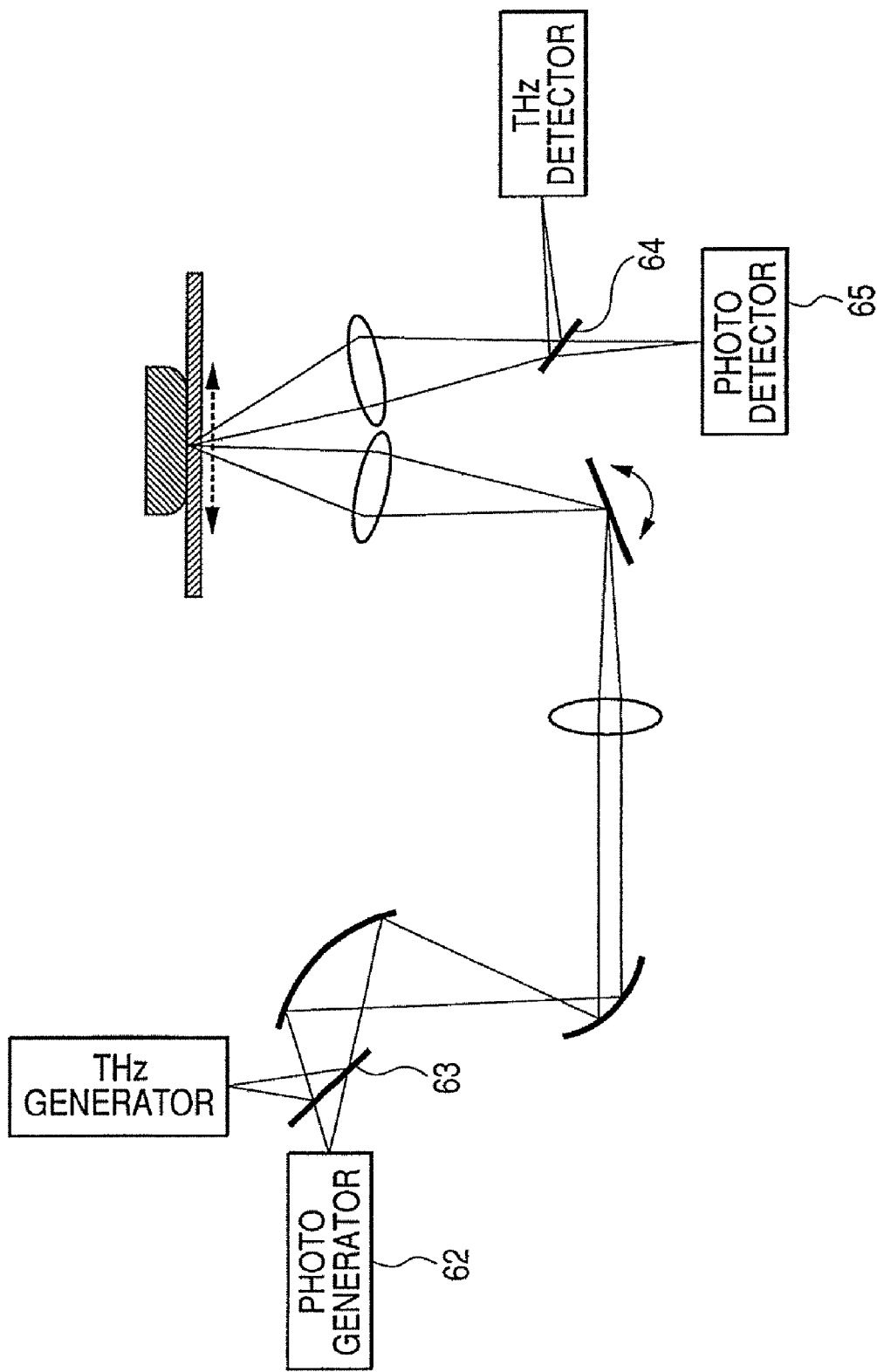
FIG. 6 is a schematic illustration of the object information acquisition apparatus of Example 2 according to the present invention.

FIG. 6 is a schematic illustration of the image acquisition apparatus of Example 2 according to the present invention. In this example, the existence or non-existence of a shoe sole on a supporting surface and, if exists, the area of existence are detected not by way of pressure but by way of light. In other words, the detection unit that detects an object of which property information is to be acquired of this example includes a unit that irradiates the area where the object is placed with light and acquiring a reflection image. Note that the components that are functionally same as those of Example 1 illustrated in FIG. 5 are not denoted by any reference symbols in FIG. 6 and will not be described here any further.

In this example, the detection unit that detects a shoe sole by means of light is coaxial with the THz optical system. Light generated from light source 62, which may typically be a halogen lamp, is transmitted through an ITO (indium tin oxide) mirror 63 and enters the THz optical system so as to irradiate the shoe sole. The light reflected by the shoe sole is then transmitted through another ITO minor 64 and enters optical detector 65. At this time, a point on the supporting surface is constantly monitored by means of light and, when a shoe is placed on the supporting surface as an object that reflects the THz-wave, the position where the shoe sole exists is identified by means of bean scanning using a galvanomirror to acquire a two-dimensional image of the object.

Thereafter, the THz-wave from the THz-wave generator two-dimensionally scans only the area of the detected shoe sole to acquire a plurality of tomographic images as information on the inside of the shoe sole. The ITO mirrors 63, 64 are adapted to exploit the property of ITO that it largely transmits light but reflects THz-waves with a high reflectance. The position of a shoe sole may be identified by light, irradiating the entire supporting surface and detecting the reflected light by means of a CCD.

Since light can be coaxially irradiated in this Example, it is possible to acquire an optical image and a THz-wave image simultaneously, outputting light and a THz-wave simultaneously. At this time, the state of propagation differs between them because a THz-wave can be diffracted with ease and hence they may show different focal positions so that a corrective operation may be required. If such is the case, a material that shows different values of permittivity for light and a THz-wave may be arranged in the region of propagation. Since there is no pressure sensor arranged on the object supporting surface in this example, it is possible to avoid a situation where the THz-wave irradiated onto an object is attenuated by such a sensor.

While a 12 mmφ beam may be used for the scanning of both the THz-wave and light as in Example 1, a linear and flat beam having a line width of 6 mm and a length of 50 mm may be used to improve the image acquisition speed. Such a beam can be produced by way of beam conversion using cylindrical lenses for the lenses 54, 55. Such a scanning scheme can be used in other examples.

Example 3

Figure 7:
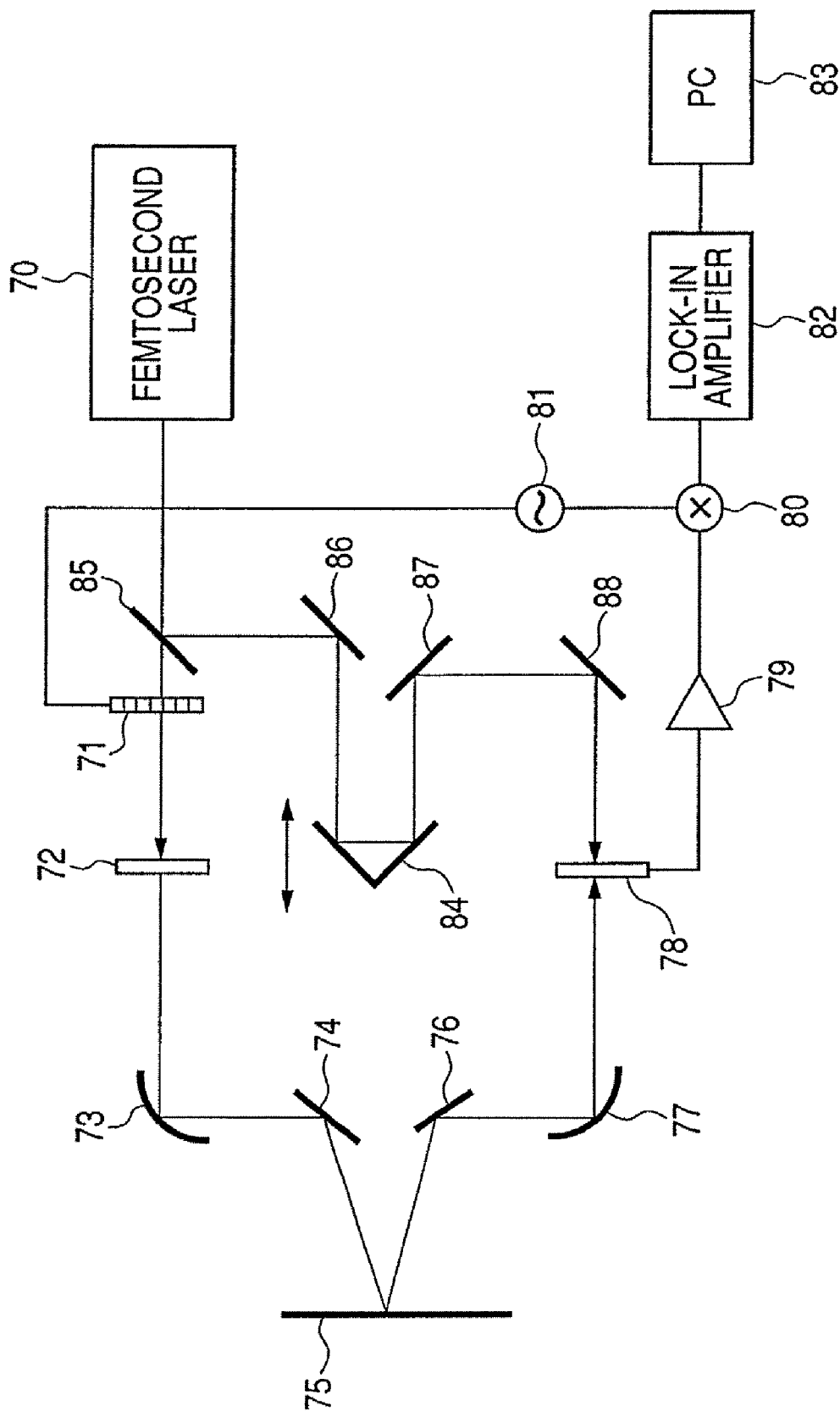
FIG. 7 is a schematic illustration of the object information acquisition apparatus of Example 3 according to the present invention.

FIG. 7 is a schematic illustration of the image acquisition apparatus of Example 3 according to the present invention.

Unlike the preceding examples, not a coherent THz-wave source but a broad band light source using a THz-wave pulse is used in this example.

The apparatus of this example can be formed by using a terahertz time domain spectroscopy (THz-TDS). With the arrangement of FIG. 7, light from laser 70 adapted to generate a ultra-short pulse of 100 femtoseconds with a wavelength of 800 nm is irradiated onto photoconductive element 72 having a dipole antenna formed on the surface of crystal such as GaAs by way of a half mirror 85 and a chopper 71 that is driven by an oscillator 81. The photoconductive element 72 generates a terahertz wave as a voltage of 10 V is applied to the gap of the antenna. The terahertz wave is irradiated onto an object supporting surface 75 through a paraboloid mirror and a mirror 74 and scattered by the shoe sole (not illustrated) placed thereon. Then, the terahertz wave is irradiated onto a photoconductive element 78 similarly by way of a mirror 76 and a paraboloid mirror 77 as in the case of the generation side element. On the other hand, an ultra-short pulse that is branched from the light emitted from the femtosecond laser 70 by means of half mirror 85 and transmitted through delay output systems 84, 86, 87 and a mirror 88 is irradiated onto the opposite surface of the photoconductive element 78. Signal wave information of the terahertz wave reflected by the plane of each level in the inside of the shoe sole is acquired by varying the delay time by means of the delay optical systems 84, 86, 87. Otherwise, the terahertz time domain spectroscopy is similar to ordinary THz-TDS devices and the signal transmitted by way of amplifier 79 and mixer 80 is processed by means of lock-in amplifier 82 and PC 83. The mirror 74 is moved to scan the shoe sole with a terahertz wave as in Example 1 to acquire two-dimensional images of planes of a plurality of levels in the inside of the object.

A terahertz-wave pulse is irradiated onto the shoe sole by way of the supporting surface 75 and detect the scattered wave from the planes of a plurality of levels in the inside of an object to acquire images in this example. In this instance, the fact that the time in which a THz wave gets to the photoconductive element 78 varies as a function of the planes of different levels relative to the direction of internal depth of the object as described above by referring to an embodiment is utilized. More specifically, the delay time of light getting to the opposite surface of the photoconductive element 78 is varied by means of the delay optical systems 84, 86, 87 to acquire fluctuation information of the terahertz wave at positions of different arrival times. In this way, it is possible to acquire a plurality of two-dimensional images that correspond to the respective planes of different levels relative to the direction of internal depth of the object.

Thus, with the mode of carrying out the present invention of this example, N in the flowchart of FIG. 2 is not the terahertz-wave generation output intensity but the delay time of the delay optical systems. If 1 ps is selected as the unit of delay time, it is possible to acquire information on the planes of different levels that are separated by several times of 100 μm in the direction of the depth of the inside of the object (depending on the material of the shoe sole).

Since a terahertz wave of a broad frequency band is used for measurement in this example, the mode of carrying out the present invention of this example provides an advantage that characteristic prohibited drugs can be checked without using a plurality of light sources.

Example 4

Figure 8:
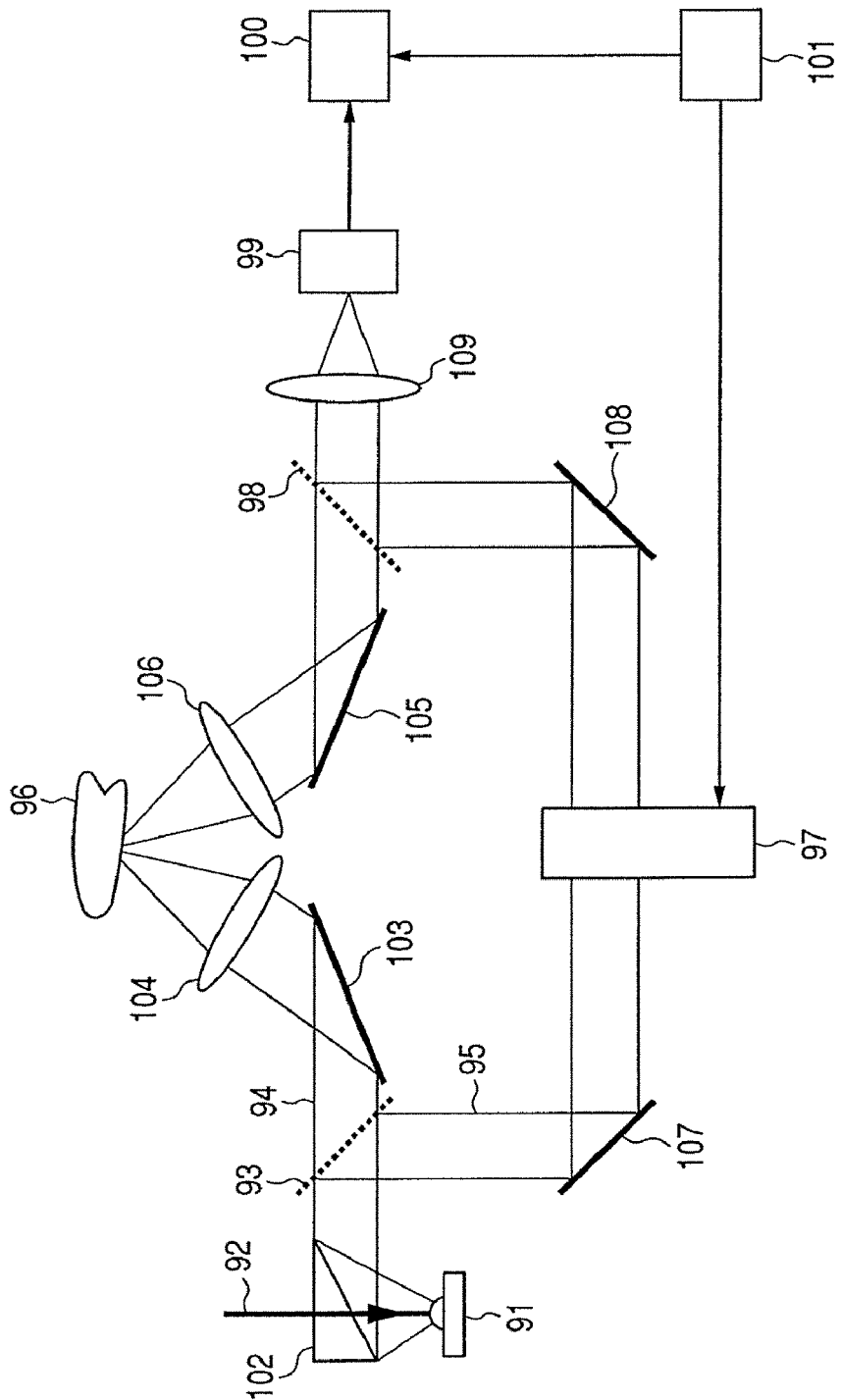
FIG. 8 is a schematic illustration of the object information acquisition apparatus of Example 4 according to the present invention.

FIG. 8 is a schematic illustration of the image acquisition apparatus of Example 4 according to the present invention.

An object information acquisition apparatus equipped with an interferometer is used in this example. More particularly, the technique of OCT (optical coherence tomography) is applied to the object information acquisition technology using a terahertz-wave domain in this example. Referring to FIG. 8, the apparatus of this example includes an electromagnetic wave generation section 91, an electromagnetic wave bifurcating section 93, an electromagnetic wave delay section 97, an electromagnetic wave coupling section 98, an electromagnetic wave detection section 99, a signal processing section 100 that serves as an information acquisition unit and a control section 101.

The electromagnetic wave generation section 91 employs a technique of generating a terahertz wave by irradiating an electromagnetic wave of a frequency not less than 30 THz as excitation light 92 onto a photoconductive element. When the photoconductive element is formed by using GaAs, for instance, an electromagnetic wave of a wavelength of 800 nm (frequency of 375 THz) is preferably used as excitation light 92. Since a broadband spectrum is necessary to improve the depth resolution for OCT, excitation light 92 is irradiated from the terahertz wave generation side of the photoconductive element as illustrated in FIG. 8. With this arrangement, the absorption of terahertz waves at the substrate is negligible, and it is possible to acquire a broad band spectrum. Of course, a technique of irradiating a semiconductor element with excitation light 92 to generate a terahertz wave can be used. If such is the case, excitation light 92 is irradiated also from the terahertz wave generation side for the same reason. The excitation light 92 used to generate a terahertz wave is reflected or scattered by the surface of the electromagnetic wave generation section 91 and emitted coaxially with the generated terahertz wave.

The electromagnetic wave emitted from the electromagnetic wave generation section 91 is reflected by an optical element 102 that reflects the electromagnetic wave and transmits the excitation light 92, and is then bifurcated into object light 94 and reference light 95 by the electromagnetic wave bifurcating section 93. A wire grid is preferably used in the electromagnetic wave bifurcating section 93 for the terahertz band.

The object light 94 is reflected by a mirror 103 and converged onto a sample (object) 96 by a lens 104. The object light 94 reflected by the sample 96 is converted into a parallel beam of light by a lens 106 and reflected by a mirror 105 to get to the electromagnetic wave coupling section 98.

On the other hand, the reference light 95 is reflected by a mirror 107 and enters the electromagnetic wave delay section 97. The electromagnetic wave delay section 97 is controlled by the control section 101 to provide the reference light 95 with a delay time. The reference light 95 provided with a delay time relative to the object light 94 is then emitted from the electromagnetic wave delay section 97 and reflected by the mirror 108 to get to the electromagnetic wave coupling section 98.

Figure 9:
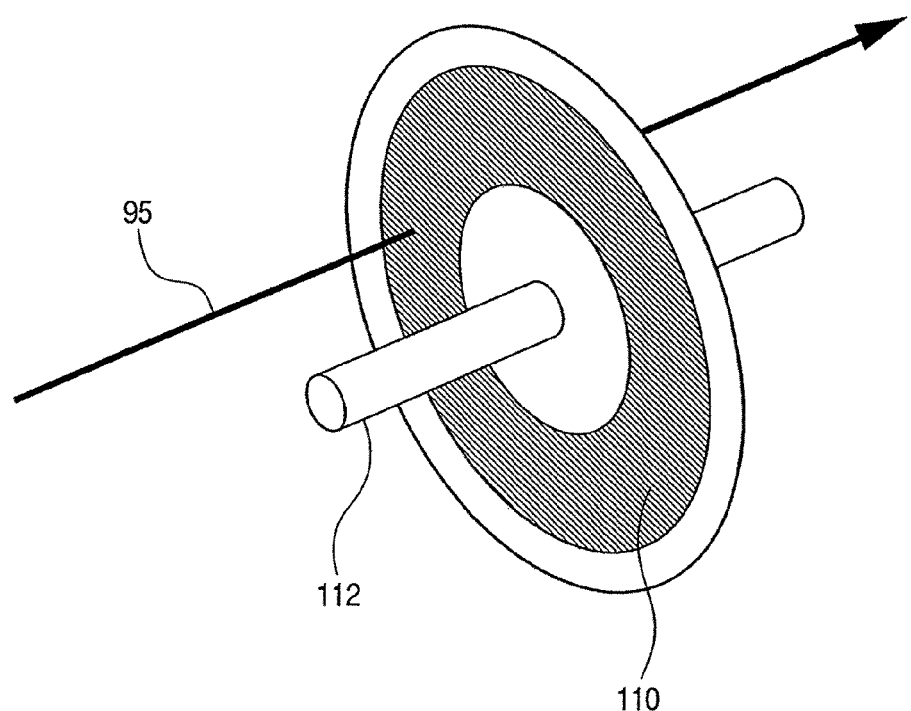
FIG. 9 is a schematic illustration of an alternative electromagnetic wave delay unit.

A rotary body that can rotate and is provided with a terahertz wave transmitting member 110 as illustrated in FIG. 9 is preferably used for the electromagnetic wave delay section 97. At least either the thickness or the refractive index of the terahertz wave transmitting member 110 is varied around the axis of rotation 112 depending on position so that the delay time of the terahertz wave 95 may be varied as the rotary body rotates around the axis of rotation 112. The electromagnetic wave delay section 97 may be provided with a plurality of such terahertz wave transmitting members. While a retro-reflector may be used for the electromagnetic wave delay section 97, it is desirable to use an electromagnetic wave delay section 97 as illustrated in FIG. 9 for the following reason. A terahertz wave is broadened when the terahertz wave is collimated to a parallel beam of the order of mm and hence the part of the electromagnetic wave delay section 97 where an electromagnetic wave is transmitted preferably has a size of about 10 mm. Then, however, the part shows an increased weight with such a size and thus, it is not easy to scan at high speed with an accurate delay time when a retro-reflector is used. On the other hand, when a rotary body as illustrated in FIG. 9 is used, it is possible to stably scan at a high rotary speed of about 6,000 rpm. Additionally, it can scan highly accurately since it involves not reciprocal drive but rotary drive.

As for the thickness of the terahertz wave transmitting member 110, the thickness is varied continuously from 2 mm to 10 mm in the sense of rotation. When polyethylene is used as material of the terahertz wave transmitting member 110, the scanning width of the quantity of delay is about 4 mm because the refractive index of polyethylene is about 1.5 in the terahertz band. Therefore, to acquire information on a sample having a refractive index of 2, for example, the scanning width and the resolution are about 1 mm and several tens of µm in the direction of the depth. A plurality of such rotary bodies may be arranged in the electromagnetic wave delay section 97. A material that shows a high transmittance relative to terahertz waves but a low transmittance relative to excitation light 92 is used for the terahertz wave transmitting member 110. Such materials include Teflon® and polyethylene. For example, high density polyethylene illustrates a transmittance of about 10% relative to excitation light of 800 nm when the thickness thereof is 2 mm. On the other hand, it illustrates a transmittance between 70% and 90% relative to terahertz waves within the range between 1 THz and 2 THz when the thickness thereof is 2 mm. Therefore, it is possible significantly to reduce the intensity of visible light or infrared rays passing through the optical path same as that of the reference light 95 relative to the terahertz wave.

The object light 94 and the reference light 95 are coupled in the electromagnetic wave coupling section 98 and subsequently conveyed to the electromagnetic wave detection section 99 by a lens 109. The electromagnetic wave intensity of the object light 94 and the reference light 95 that are coupled is detected as interference signal by the electromagnetic wave detection section 99. Examples of devices that can be used for the electromagnetic wave detection section 99 include a DLATGS detector, a Golay cell and a bolometer.

The excitation light 92 that is reflected or scattered by the electromagnetic wave generation section 91 gets to the electromagnetic wave detection section 99 by way of the route same as the terahertz wave in addition to the latter. The excitation light 92 operates as noise in terahertz-OCT to reduce the resolution in the direction of depth of the object. However, it is possible to reduce the interference signal component of the excitation light 92 detected by the electromagnetic wave detection section 99 in this example because the reduction ratio of the intensity of the excitation light 92 is large relative to the reduction ratio of the intensity of the terahertz wave in the electromagnetic wave delay section 97. Thus, it is possible to raise the resolution in the direction of the depth. Of course, the technique of providing the electromagnetic wave bifurcating section 93, the electromagnetic wave coupling section 98, the electromagnetic wave detection section 99, the lenses 104, 106, 109 and the mirrors 103, 105, 107, 108 with such a filter feature may be used. By providing one or more than one optical element contained in the apparatus with such a feature, it is possible to reduce the loss of the terahertz wave as compared with an arrangement of adding a new filter element, and thus one can minimize the number of elements of the apparatus. For example, when a 2 mm-thick polyethylene plate is added as filter element, the loss of the terahertz wave in the range between 1 THz and 2 THz is increased by about 10% to 30% as compared with this example.

An arrangement for separating the excitation light 92 and the terahertz wave by means of the surface structure of some of the optical elements may be employed as a technique of reducing the detection intensity of the excitation light 92 relative to that of the terahertz wave. More specifically, optical elements including the electromagnetic wave delay section 97, the electromagnetic wave bifurcating section 93, the electromagnetic wave coupling section 98, the electromagnetic wave detection section 99, the lenses and the mirrors are provided with a grating or a coarse surface that corresponds to the wavelength of the excitation light 92. A pitch of about 1 µm may typically be used for the grating or the coarse surface. Since a terahertz wave typically has a wavelength of about 300 µm, a grating or a coarse surface having such a dimensional element does not practically influence the terahertz wave. Therefore, it is possible efficiently to separate the excitation light 92 and the terahertz wave. Thus, in this way, it is possible to reduce the excitation light by differentiating the transmission characteristic or the reflection characteristic thereof relative to at least part of electromagnetic waves found between 30 GHz and 30 THz and at least part of electromagnetic waves found at or above 30 THz for at least one of the optical elements of the apparatus.

Figure 10A:
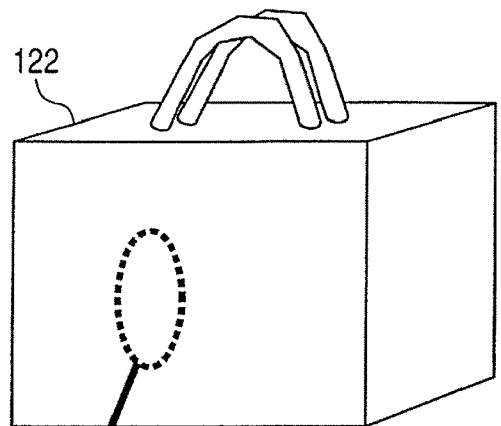
FIGS. 10A and 10B are schematic illustration of a drug hidden in a gap of leathers of a bag.
Figure 10B:
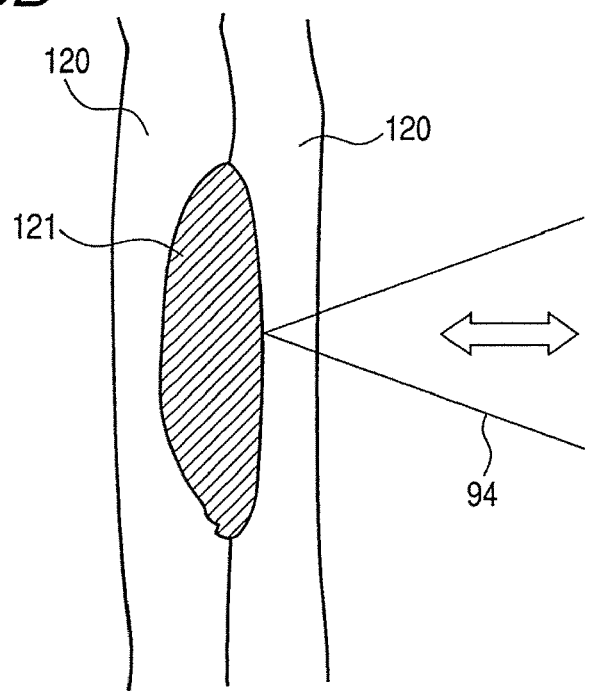

Any of the instruments described in the examples can be applied to baggage inspections in airports and other facilities. FIG. 10A schematically illustrates a bag 122 and FIG. 10B is a schematic cross-sectional view of a drug 121 hidden in a gap of leathers 120 of the bag of FIG. 10A. As a terahertz wave is irradiated onto the bag by means of any of the apparatus described in the examples and the corresponding method described above by referring to the embodiment and Examples 1 through 3, the terahertz wave is reflected by the surface of the leathers 120 and the drug 121. The reflected waves interfere with reference light and enable to identify the positions of reflection so that it is possible to acquire tomographic images and detect the hidden drug. The apparatus is preferably so arranged that the apparatus can acquire information both in the direction of depth and in the direction of planes perpendicular to the depth by way of beam scanning or object scanning.

As described above, an object information acquisition apparatus equipped with an interferometer and described in the related example can reduce the noise attributable to excitation light so that it is possible to acquire tomographic images in the direction of depth with a high resolution. Additionally, since the apparatus is provided with a feature of reducing the interference component of excitation light without adding any optical element to the apparatus, it is possible to minimize the number of elements of the apparatus and make the apparatus compact.

While image acquisition apparatus for mainly examining the inside of a shoe sole or a bag is described in the examples, the present invention is equally applicable to examination of the inside of hand-carry baggage, a distribution item or a box. It is desirable to optimize the intensity of terahertz wave according to information that needs to be acquired in the direction of depth of the inside of the object of examination.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2006-275898, filed Oct. 10, 2006 and 2007-186382, filed Jul. 18, 2007, which are incorporated by reference herein in their entirety.

The invention claimed is:

1. An object information acquisition apparatus for acquiring information on the inside of an object, the apparatus comprising:
- an electromagnetic wave generation unit capable of outputting an electromagnetic wave containing a frequency component of part of the frequency range between 30 GHz and 30 THz and of changing an output intensity of the electromagnetic wave;
- an irradiation unit that irradiates the electromagnetic wave to the object;
- a scanning unit that changes the relative position of the irradiated electromagnetic wave and the object; and
- a detection unit that detects the electromagnetic wave transmitted through or reflected by the object as a result of interaction of the object and the electromagnetic wave,
- the apparatus being adapted to acquire tomographic information of planes of different levels in the inside of the object relative to the direction of depth thereof in the region of the object of information acquisition according to a signal detected by the detection unit by combining the operation of changing the relative position by the scanning unit and the operation of changing the intensity of the electromagnetic wave by the electromagnetic wave generation unit.

2. The object information acquisition apparatus according to claim 1, wherein the electromagnetic wave generation unit has at least two coherent light sources, each oscillating with a single frequency in the frequency range between 30 GHz and 30 THz, for different frequencies.

3. The object information acquisition apparatus according to claim 1, wherein at least one optical element contained in the apparatus illustrates a transmission characteristic or a reflection characteristic relative to at least part of electromagnetic wave found between 30 GHz and 30 THz that is differentiated from a transmission characteristic or a reflection characteristic, whichever appropriate, relative to at least part of an electromagnetic wave found at or above 30 THz for the at least one optical element of the apparatus.

4. The object information acquisition apparatus according to claim 1, further comprising:
- a transmission unit that detects, if any, the existence of a target object of examination contained in an object from the acquired tomographic information of the plane of a level in the direction of depth of the object and transmits a signal providing notification of the existence thereof.

5. The object information acquisition apparatus according to claim 1, further comprising:
- a detection unit that detects the region of an object of acquisition of tomographic information.

6. An object information acquisition apparatus for acquiring information on the inside of an object, the apparatus comprising:
- an electromagnetic wave generation unit capable of outputting an electromagnetic wave containing a frequency component of part of the frequency range between 30 GHz and 30 THz;
- an irradiation unit that irradiates the electromagnetic wave to the object;
- a scanning unit that changes the relative position of the irradiated electromagnetic wave and the object;
- a detection unit that detects the electromagnetic wave transmitted through or reflected by the object as a result of interaction of the object and the electromagnetic wave; and
- a delay unit that changes a delay time between the timing of outputting the electromagnetic wave of the electromagnetic wave generation unit and the timing of detecting the electromagnetic wave by the detection unit,
- the apparatus being adapted to acquire tomographic information of planes of different levels in the inside of the object relative to the direction of depth thereof in the region of the object of information acquisition according to a signal detected by the detection unit by combining the operation of changing the relative position by the scanning unit and the operation of changing the delay time by the delay unit.

7. The object information acquisition apparatus according to claim 6, wherein the delay unit includes a rotatable transmitting body capable of transmitting the electromagnetic wave and the delay time is made to vary by rotating the transmitting body so as to vary at least either the thickness or the refractive index of the region of the transmitting body for transmitting the electromagnetic wave.

8. The object information acquisition apparatus according to claim 6, wherein at least one optical element contained in the apparatus illustrates a transmission characteristic or a reflection characteristic relative to at least part of electromagnetic wave found between 30 GHz and 30 THz that is differentiated from a transmission characteristic or a reflection characteristic, whichever appropriate, relative to at least part of an electromagnetic wave found at or above 30 THz for the at least one optical element of the apparatus.

9. The object information acquisition apparatus according to claim 6, further comprising:
- a transmission unit that detects, if any, the existence of a target object of examination contained in an object from the acquired tomographic information of the plane of a level in the direction of depth of the object and transmits a signal providing notification of the existence thereof.

10. The object information acquisition apparatus according to claim 6, further comprising:
- a detection unit that detects the region of an object of acquisition of tomographic information.

11. An object information acquisition apparatus for acquiring information on the inside of an object, the apparatus comprising:
- an electromagnetic wave generation unit capable of outputting an electromagnetic wave containing a frequency component of part of the frequency range between 30 GHz and 30 THz;
- an electromagnetic wave bifurcating unit that bifurcates the electromagnetic wave into reference light and object light;
- an irradiation unit that irradiates the object light to the object;
- a scanning unit that changes the relative position of the irradiated object light and the object;
- a delay unit arranged on either or both of the light path of the reference light and that of the object light to change a relative delay time between the reference light and the object light;
- an electromagnetic wave coupling unit that couples the object light transmitted through or reflected by the object as a result of interaction with the object and the reference light provided with the relative delay time to the object light by the delay unit; and a detection unit that detects an interference signal of the reference light and the object light coupled by the electromagnetic wave coupling unit, the apparatus being adapted to acquire tomographic information of planes of different levels in the inside of the object relative to the direction of depth thereof in the region of the object of information acquisition according to a signal detected by the detection unit by combining the operation of changing the relative position by the scanning unit and the operation of changing the delay time by the delay unit.

12. The object information acquisition apparatus according to claim 11, wherein the delay unit includes a rotatable transmitting body capable of transmitting the electromagnetic wave and the delay time is made to vary by rotating the transmitting body so as to vary at least either the thickness or the refractive index of the region of the transmitting body for transmitting the electromagnetic wave.

13. The object information acquisition apparatus according to claim 11, wherein at least one optical element contained in the apparatus illustrates a transmission characteristic or a reflection characteristic relative to at least part of electromagnetic wave found between 30 GHz and 30 THz that is differentiated from a transmission characteristic or a reflection characteristic, whichever appropriate, relative to at least part of an electromagnetic wave found at or above 30 THz for the at least one optical element of the apparatus.

14. The object information acquisition apparatus according to claim 11, further comprising:
a transmission unit that detects, if any, the existence of a target object of examination contained in an object from the acquired tomographic information of the plane of a level in the direction of depth of the object and transmits a signal providing notification of the existence thereof.

15. The object information acquisition apparatus according to claim 11, further comprising:
a detection unit that detects the region of an object of acquisition of tomographic information.

16. An object information acquisition method for acquiring information on the inside of an object, the method comprising:
a first output step of outputting an electromagnetic wave containing a frequency component of part of the frequency range between 30 GHz and 30 THz with a predetermined output power;
a first scanning step of irradiating object light produced by bifurcating the electromagnetic wave of the first output step, while changing the relative position thereof to the region of existence of the object;
a first detection step of defining a relative delay time between reference light produced by bifurcating the electromagnetic wave of the first output step and the object light as a first time at each scanning position of the first scanning step and detecting an interference signal of the reference light and the object light produced as a result of coupling the object light transmitted through or reflected by the object as a result of interaction with the object and the reference light provided with the relative delay time;
a second output step of outputting the electromagnetic wave output in the first output step with the predetermined output power;
a second scanning step of irradiating object light produced by bifurcating the electromagnetic wave of the second output step, while changing the relative position thereof to the region of existence of the object;
a second detection step of defining a relative delay time between reference light produced by bifurcating the electromagnetic wave of the second output step and the object light as a second time at each scanning position of the second scanning step and detecting an interference signal of the reference light and the object light produced as a result of coupling object light transmitted through or reflected by the object as a result of interaction with the object and the reference light provided with the relative delay time; and
a tomographic information acquisition step of processing the signal detected in the first detection step and the signal detected in the second detection step and acquiring tomographic information of planes of different levels relative to the direction of internal depth of the object within the region of the object for acquiring information thereof.

17. The object information acquisition method according to claim 16, further comprising:
a transmission step of, after detecting, if any, the existence of a target object of examination contained in an object in the tomographic information acquisition step, transmitting a signal providing notification of the existence thereof.

18. An object information acquisition method for acquiring information on the inside of an object, the method comprising:
an output step of outputting an electromagnetic wave containing a frequency component of part of the frequency range between 30 GHz and 30 THz;
a scanning step of irradiating the electromagnetic wave, while changing the relative position thereof to the region of existence of the object;
a detection step of varying an output power of the electromagnetic wave from a predetermined output power, and detecting the electromagnetic wave transmitted through or reflected by the object as a result of interaction with the object at each time of varying the output power;
a tomographic information acquisition step of subjecting a signal detected in the detection step to a process including an arithmetic process of determining a variations of the signal and acquiring tomographic information of at least a plane of a level relative to the direction of internal depth of the object within the region of the object for acquiring information thereof.

19. The object information acquisition method according to claim 18, further comprising:
a transmission step of, after detecting, if any, the existence of a target object of examination contained in an object in the tomographic information acquisition step, transmitting a signal providing notification of the existence thereof.

20. An object information acquisition method for acquiring information on the inside of an object, the method comprising:
an output step of outputting an electromagnetic wave containing a frequency component of part of the frequency range between 30 GHz and 30 THz with a predetermined output power;
a scanning step of irradiating the electromagnetic wave, while changing the relative position thereof to the region of existence of the object;
a detection step of changing a delay time between the timing of outputting the electromagnetic wave and the timing of detecting the electromagnetic wave from a predetermined time at each scanning position of the scanning step and detecting the electromagnetic wave transmitted through or reflected by the object as a result of interaction with the object at each time of changing the delay time; and
a tomographic information acquisition step of processing a signal detected in the detection step and acquiring tomographic information of at least a plane of a level relative to the direction of internal depth of the object within the region of the object for acquiring information thereof.

21. The object information acquisition method according to claim 20, further comprising:
a transmission step of, after detecting, if any, the existence of a target object of examination contained in an object in the tomographic information acquisition step, transmitting a signal providing notification of the existence thereof.

* * * * *